(12) United States Patent
Haras

(10) Patent No.: US 7,835,497 B2
(45) Date of Patent: Nov. 16, 2010

(54) METHOD FOR AUTOMATIC EVALUATION OF SCAN IMAGE DATA RECORDS

(75) Inventor: Gabriel Haras, Mücke (DE)

(73) Assignee: Siemens Aktiengesellschaft, Munich (DE)

( * ) Notice: Subject to any disclaimer, the term of this patent is extended or adjusted under 35 U.S.C. 154(b) by 284 days.

(21) Appl. No.: 12/071,105

(22) Filed: Feb. 15, 2008

(65) Prior Publication Data

US 2008/0212741 A1    Sep. 4, 2008

(30) Foreign Application Priority Data

Feb. 16, 2007   (DE) .................. 10 2007 007 803

(51) Int. Cl.
*H05G 1/64* (2006.01)
(52) U.S. Cl. ...................................... 378/98
(58) Field of Classification Search ............. 378/98; 382/128
See application file for complete search history.

(56) References Cited

U.S. PATENT DOCUMENTS

| | | | |
|---|---|---|---|
| 5,371,778 A * | 12/1994 | Yanof et al. ..................... 378/4 |
| 2002/0054662 A1 * | 5/2002 | Verdonck et al. .............. 378/62 |
| 2003/0086596 A1 * | 5/2003 | Hipp et al. .................. 382/128 |
| 2004/0101175 A1 * | 5/2004 | Yarger et al. ................ 382/128 |
| 2004/0101183 A1 * | 5/2004 | Mullick et al. ............. 382/131 |
| 2004/0122309 A1 * | 6/2004 | Deller et al. ................ 600/425 |
| 2004/0240715 A1 * | 12/2004 | Wicker et al. ............... 382/128 |
| 2004/0252872 A1 * | 12/2004 | Tsai et al. .................... 382/131 |
| 2006/0002630 A1 * | 1/2006 | Fu et al. ...................... 382/294 |
| 2006/0110017 A1 | 5/2006 | Tsai et al. |
| 2006/0122487 A1 * | 6/2006 | Tatebayashi et al. ........ 600/410 |
| 2007/0038070 A1 | 2/2007 | Tank |
| 2007/0121778 A1 * | 5/2007 | Shen et al. ..................... 378/4 |

OTHER PUBLICATIONS

W.A. Kalender et al. "Bone Mineral Measurement: Automated Determination of Midvertebral CT Section", Radiology vol. 168, No. 1, 1988, Seiten 219 bis 221, Others.
German Office Action issued Nov. 8, 2007.

* cited by examiner

*Primary Examiner*—Edward J Glick
*Assistant Examiner*—Alexander H Taningco
(74) *Attorney, Agent, or Firm*—Harness, Dickey & Pierce, P.L.C.

(57) ABSTRACT

A method is disclosed for automatic evaluation of tomographic image data records of a patient. In at least one embodiment, a scan of a patient being carried out using a tomography system, a three-dimensional tomographic image data record of at least a part of the patient is reconstructed, the spatial position and orientation of vertebrae is then determined, and medically relevant slice areas are determined automatically with a previously defined diagnostic question relating to the position, orientation and extent of spinal column diagnosis. Finally, with slice images of the relevant slice areas are produced and displayed. In addition, in at least one embodiment, a tomography system includes a computation unit with a memory for program code, with the memory also being used to store a program code which carries out the method steps of the method according to at least one embodiment of the invention during operation.

34 Claims, 5 Drawing Sheets

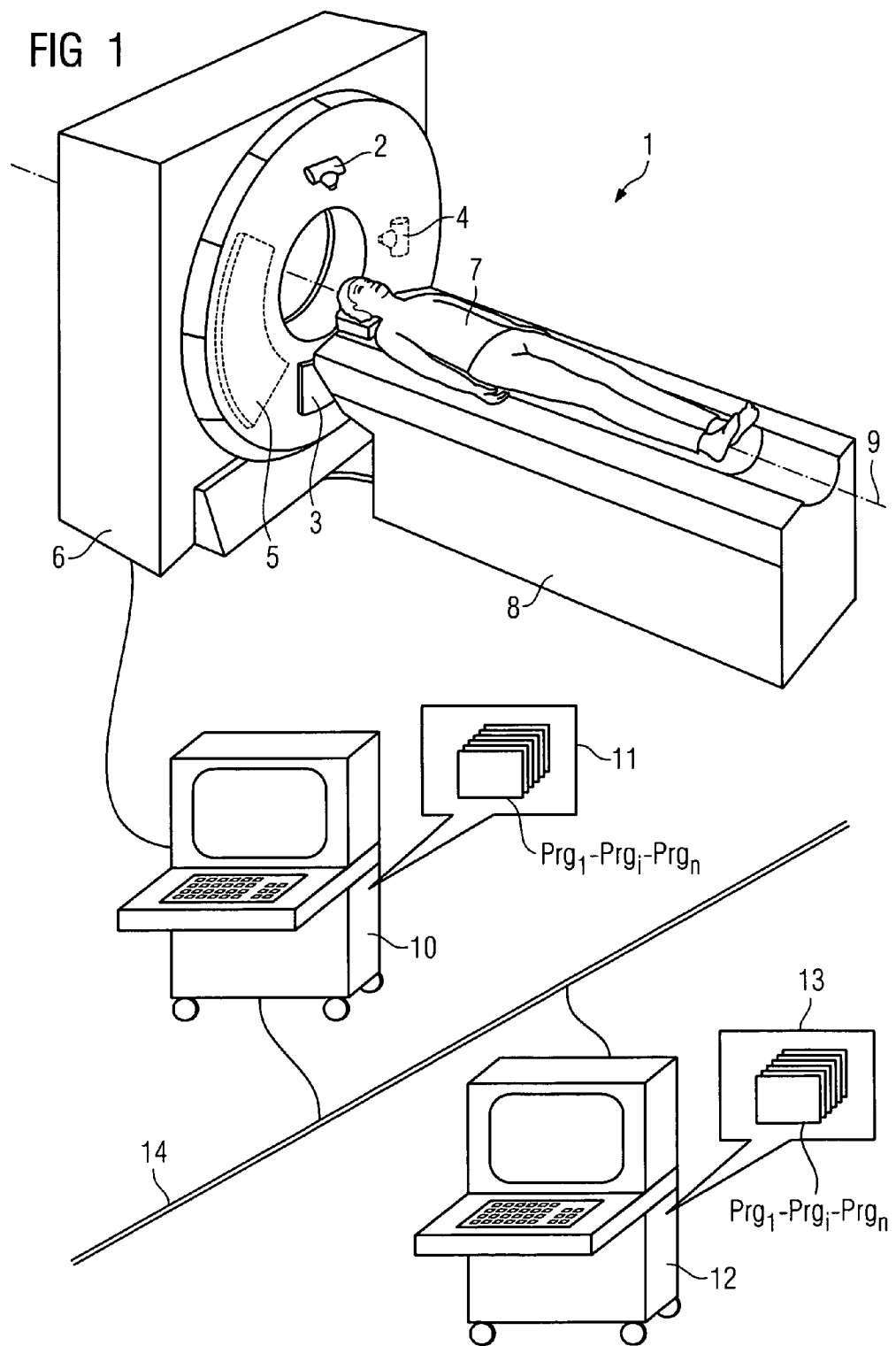

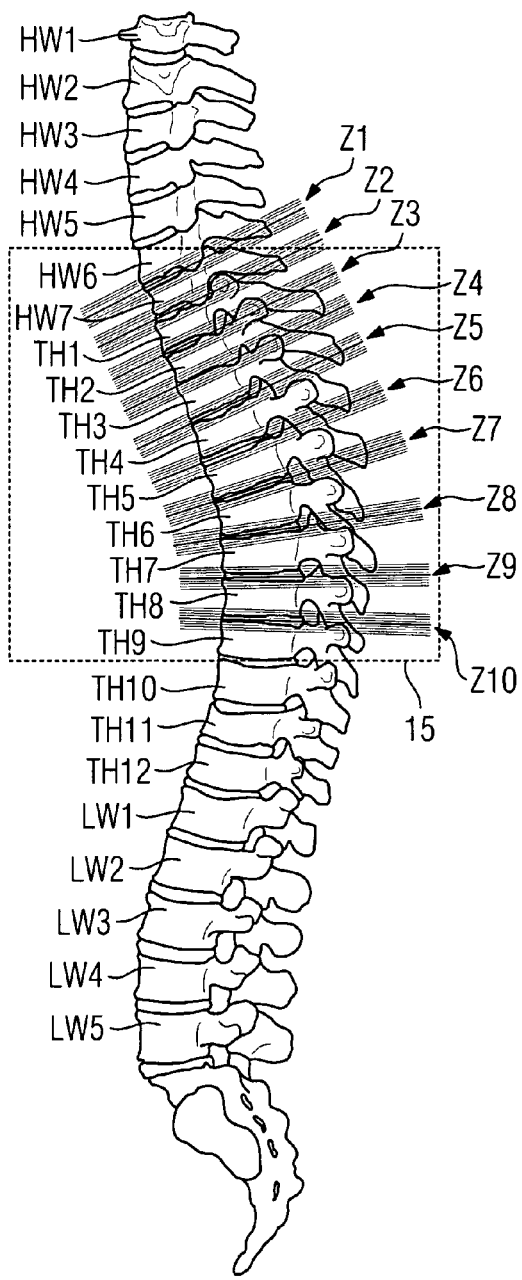
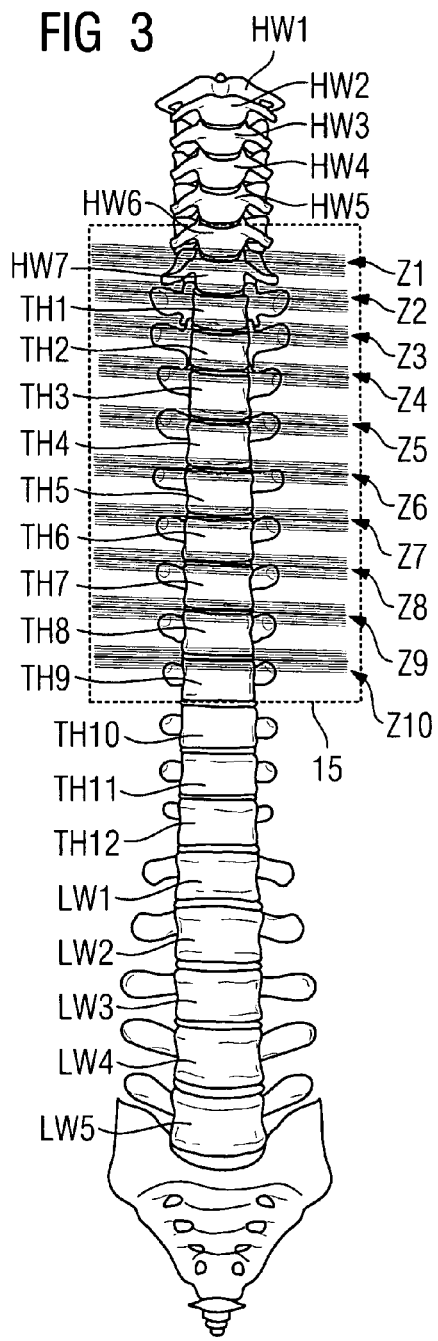

METHOD FOR AUTOMATIC EVALUATION OF SCAN IMAGE DATA RECORDS

PRIORITY STATEMENT

The present application hereby claims priority under 35 U.S.C. §119 on German patent application number DE 10 2007 007 803.1 filed Feb. 16, 2007, the entire contents of which is hereby incorporated herein by reference.

FIELD

Embodiments of the invention relate in general to a method for automatic evaluation of tomographic image data records of a patient; for example with respect to the spatial position and orientation of vertebrae and the production of slices in the correct orientation in the area of the vertebrae and in the area of the spaces between the vertebrae.

BACKGROUND

It is generally known for slices to be obtained automatically in the area of the spinal column of a patient on the basis of previously determined tomographic data records, with the orientation and position of the individual vertebrae also being automatically identified, and appropriate slices defined, in the tomographic data records.

By way of example, reference is made in these contexts to the document *W. A. Kalender, H. Brestowsky, D. Felsenberg, Radiology Vol.* 168 No. 1, 1988, pages 219 to 221, Bone Mineral Measurement: Automated Determination of Midvertebral CT Section.

One problem with the already known methods for automatic evaluation of tomographic data records is that the manual work required by the operator is extremely complex. Nowadays, about five minutes is required for definition of the planes of the slice images in the area of the spinal column for each spinal column section, that is to say for example for each cervical spine area, each thoracic spine area, or each lumbar spine area. If a plurality of such sections are required for consideration of the spinal column, the time required is multiplied in a corresponding manner.

SUMMARY

In at least one embodiment of the invention, a method is disclosed which considerably reduces the time required to produce such slice images.

The inventor therefore proposes, in at least one embodiment, a method for automatic evaluation of tomographic image data records of a patient, comprising:
  scan of a patient by way of a tomography system,
  reconstruction of a three-dimensional tomographic image data record of at least a part of the patient,
  determination of the spatial position and orientation of vertebrae,
  automatic determination of medically relevant slice areas in accordance with a previously defined diagnostic question relating to the position, orientation and extent for spinal column diagnosis, and
  creation and display of slice images of these relevant slice areas.

In one advantageous variant of at least one embodiment of the method described above, the inventor proposes that the relevant slice images be stored on a patient-specific basis. This makes it possible to view the existing documentation once again where necessary, and to satisfy the documentation requirements. However, one problem in this case is also that enormous amounts of data are very quickly created because of the relatively high memory requirement for each slice image, and this data must be stored on a patient-specific basis. In order to improve this situation, the inventor proposes that just the position, orientation and the extent of the relevant slice images be stored on a patient-specific basis. In this case, it is particularly advantageous for a reference to the tomographic image data record that is used to be stored, so that the slice images, which were originally created automatically, can be reproduced at any time from the orientation information relating to the slice images.

Another variant of at least one embodiment proposes that, in addition to the orientation of the relevant slice images, at least one reference to the original detector data from which the tomographic image data record that is used has been reconstructed be stored. This makes it possible to use the original detector data of the patient scan to reconstruct the tomographic image data record, possibly to reconstruct it in different conditions, and nevertheless to reproduce the slice images at the previously defined point, in which case further image information can additionally be found in the relevant slice images in the case of a reconstruction and when subject to different constraints.

Specifically, with regard to the automatic creation of the relevant slice images, the inventor proposes that different areas be considered with the correct area being searched for in each case by the evaluation method when defining a diagnostic question, and with the relevant slice planes then being determined. In this context, it should be noted that the subsequently used annotations of the slice planes in each case relate to the axes of the anatomical structure under consideration, that is to say for example the vertebra or vertebrae or the entire spinal column under consideration, and not to the major axes of the patient or of the CT. This avoids confusion which, for example, could occur in the event of major curvature of the spinal column and in the case of the inclined orientation associated with this relative to the major axes of the patient or of the CT.

On the basis of an idea of at least one embodiment of the invention, it is also proposed that, when defining a diagnostic question for which the intervertebral area possibly with adjacent dorsal and ventral plates of the adjacent vertebrae is important, an embodiment of the method comprises:
  Determination of the orientation of the ventral plate of a vertebra located at the top,
  Determination of the orientation of the dorsal plate of a vertebra located underneath,
  Determination of the orientation of the angle-bisecting plane (=angle-bisecting intervertebral plane) between a previously determined ventral and dorsal plate, and
  Calculation of a multiplicity of preferably equidistant slice image areas (=intervertebral slice image area) parallel to the angle-bisecting plane.

In this case, it is advantageous if, the two outer intervertebral slice image areas each intersect the adjacent vertebra. Furthermore, it is also advantageous if at least one slice image area is additionally calculated which runs parallel to and through the dorsal plate of the lower vertebra, or through the ventral plate of the upper vertebra.

In a further embodiment of the method, the inventor proposes that, when defining a diagnostic question in which the structure of a vertebra is itself important, an embodiment of the method comprises:
  Determination of the position, of the end points of the transverse processes of the selected vertebra, Determination of the planes of the dorsal plate and ventral plate and of the angle-bisecting plane (axial interplate plane) between the dorsal plate and the ventral plate, Determination of the plane (=coronal plane) parallel to the connecting line between the ends of the transverse processes and perpendicular to the interplate plane, and Calculation of a multiplicity of preferably equidistant slice image areas parallel to the coronal plane (=coronal vertebra slice image areas).

In this case, it is particularly advantageous for the coronal vertebra slice image areas to be formed such that they completely surround the vertebra.

If axial slices are particularly important for the diagnostic question relating to the structure of the vertebra, then the inventor in this case proposes that an embodiment of the method comprises:

determination of the planes of the dorsal plate and ventral plate and of the angle-bisecting plane (=axial interplate plane) between the dorsal plate and the ventral plate, and calculation of a multiplicity of preferably equidistant slice image areas parallel to the axial interplate plane (=axial vertebra slice image areas).

In this case, it is also worthwhile for the multiplicity of axial vertebra slice image areas to completely surround the vertebra.

If sagittal slices of the vertebra itself are also significant for the diagnostic question, then the inventor proposes that an embodiment of the method comprises:

Determination of the longitudinal axis of the spinous process of the selected vertebra, Determination of the planes of the dorsal plate and ventral plate and of the angle-bisecting plane (=axial interplate plane) between the dorsal plate and the ventral plate, Determination of the plane (=sagittal vertebral plane) at right angles to the axial interplate plane and parallel to the longitudinal axis of the spinous process, and Calculation of a multiplicity of preferably equidistant slice image areas parallel to the sagittal vertebral plane (=sagittal vertebra slice image areas).

In the case of slice images such as these, it is advantageous for these slice images to completely surround the vertebra with the exception of the transverse processes. In addition, at least one of the sagittal vertebra slice image areas should advantageously run through the spinous process itself.

For diagnosis of the spinal canal, the inventor proposes that an embodiment of the method comprises:

Determination of the position of the center of the spinal canal, in a plurality of selected vertebrae, Determination of the position of the longitudinal axes of the spinous processes of the selected vertebrae, Determination of the center plane (=central sagittal spinal plane) through the longitudinal axis of the spinous processes and the positions of the center of the spinal canals of the selected vertebrae, and Calculation of at least one slice image area along the central sagittal spinal plane.

With this selection and sizing of the slice image areas, it is advantageous for these sagittal slices to be oriented parallel to the central sagittal spinal plane.

If the spinal column overall is also important for the diagnostic question, then an embodiment of the method comprises:

Determination of the position of the center of the selected vertebrae,

Determination of the position of the longitudinal axes of the spinous processes of the selected vertebrae, Determination of the central plane (=central sagittal vertebral plane) through the longitudinal axis of the spinous processes and the positions of the center of the selected vertebrae, and Calculation of at least one slice image area along the central sagittal vertebral plane.

In this case as well, a multiplicity of preferably equidistant sagittal slice image areas should be oriented parallel to the central sagittal vertebral plane.

Furthermore, with respect to the sizing of the slice image areas, it is generally proposed that these slice image areas be configured such that the vertebra or vertebrae to be displayed is or are displayed such that it or they fill at least 50% of the format, and preferably at least 75% of the format. Since the CT records and the corresponding image display generally use image formats of 512×512 pixels, it is particularly advantageous to include the vertebrae to be considered such that they relatively fill the format, since these are the only conditions which ensure adequate detail resolution.

A further improvement to the method according to at least one embodiment of the invention also proposes that the vertebra are automatically annotated in at least one topogram and/or in the three-dimensional tomographic image data record. In this case, the annotation of the vertebrae can be transferred to the vertebrae which are shown in the slice area images, so that the respectively displayed vertebrae, or the space between two vertebrae is indicated in the display of a slice area image.

It is also proposed that the vertebrae be annotated automatically in response to a manual definition of a vertebra. This is particularly relevant, for example, when just one part of the patient has been scanned and in consequence the start or end of the spinal column cannot be seen, so that automatic numbering is possible only with great difficulty, or with a high error rate. For example, in this case, a specific vertebra can be marked on the screen and the number of this vertebra can be entered by the operator, with the remaining vertebrae in the scanned area being annotated automatically by the machine on the basis of this input.

In addition, the inventor also proposes that in at least one embodiment, for viewing the slice image areas, the operator be provided with the capability to scroll through the automatically determined planes, preferably using a mouse wheel, on a display, in which case it is particularly advantageous, while scrolling through, to indicate the currently displayed slice in an overview representation of the spinal column, as well, in addition to the view of the currently selected slice image area. The scrolling-through process does not take place in this case, as known per se, on a plane but, instead, the plane of the automatically determined slice image areas is in each case displayed. This plane is tilted appropriately by scrolling through over a plurality of vertebrae, corresponding to the orientation of the vertebrae in the patient's body. This can be done either by calling up the automatically determined slice image areas sequentially from a memory, or by in each case recalculating the slice image areas from the patient volume data on the basis of previously stored orientation definitions of the slice image areas.

In addition to the method described above, the inventor also proposes in at least one embodiment, an X-ray CT system having a computation and control unit with a memory for program code, in which case the memory of the computation and control unit is used to store program code which carries out the method steps according to at least one embodiment of one of the above-described methods during operation.

In the situation in which the detector data, or the image data calculated from it, is already available, then this corresponding program code can also be stored in a simple screen workstation without there necessarily being any need for a direct link to an X-ray CT system. This allows appropriate processing of the CT image data without interfering with the CT examination procedure.

BRIEF DESCRIPTION OF THE DRAWINGS

Embodiments of the invention will be described in more detail with the aid of the figures in the following text, with the figures illustrating only those features which are necessary for understanding of embodiments of the invention. The following reference symbols are used in this case: 1: CT system; 2: first X-ray tube; 3: first detector; 4: second X-ray tube; 5: second detector; 6: gantry housing; 7: patient; 8: movable patient couch; 9: system axis of the CT system; 10: control and computation unit; 11: memory; 12: computer workstation; 13: computer workstation memory; 14: data bus; 15: scan area; 16: sagittal slice plane relative to the patient; 17: center line of the vertebral bodies of a spinal column; 18: spinal canal; a1 to a5: distance lines between the dorsal plate and the ventral plate; D: spinous process; $E_B$: plane of the ventral plate of a vertebra; $E_D$: plane of the dorsal plate of a vertebra; HW1 to HW7: cervical vertebrae; K: coronal section plane along the link between the end points of the transverse processes of a vertebra; LW1 to LW5: lumbar vertebrae; M: central slice plane between the dorsal plate and the ventral plate of a vertebra; $Prg_1$-$Prg_i$-$Prg_n$: computer programs; $Q_L$: transverse process, left; $Q_R$: transverse process, right; S: sagittal slice plane through the longitudinal axis of the spinous process of a vertebra; $S_f$: coronal slice area; $S_k$: coronal slice image area; $S_s$: sagittal slice area; $S_a$: axial slice area; TH1 to TH12: thoracic vertebrae; $W_k$: vertebral bodies; Z: central slice plane between the dorsal plate and the ventral plate of two adjacent vertebrae; Z1 to Z10: intermediate vertebral bodies—slice image areas.

In detail, in the figures:

FIG. 1: shows a schematic illustration of a CT for carrying out the method according to an embodiment of the invention;

FIG. 2: shows a side view of a complete spinal column with a scan area and automatically positioned axial slices;

FIG. 3: shows a coronal view of the spinal column from FIG. 2;

DETAILED DESCRIPTION OF THE EXAMPLE EMBODIMENTS

Figure 4:
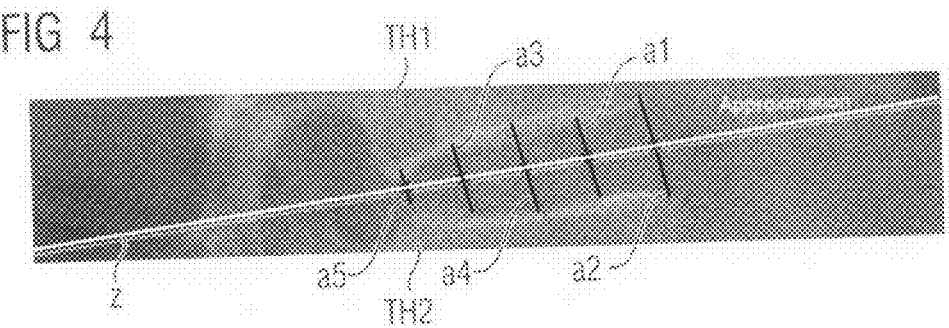
FIG. 4: shows an illustration of an example of a variant for determining a central slice plane between two vertebrae.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an example of a development of a tomography system, in this case a CT system 1, by which the method according to an embodiment of the invention can be carried out. The CT system 1 has a gantry housing 6 in which a gantry, which is not illustrated in any more detail here, is located and on which at least one focus-detector system, comprising an X-ray tube 2 and an opposite detector 3, possibly with a second focus-detector system as well, in this case represented by the X-ray tube 4 and the opposite detector 5, are located. The focus-detector systems are rotated with the aid of the gantry during the scan, while the patient 7 is moved on a movable patient couch 8 along the system axis 9 through the scan area of the focus-detector systems, thus resulting in a spiral scan relative to the patient.

The operation of the CT system 1 is monitored by a control and computation unit 10 which has a memory 11 in which programs $Prg_1$ to $Prg_n$ are responsible for operation of the installation, evaluation of the detector data and reconstruction of the tomographic data records. According to an embodiment of the invention, this program pool also includes a program $Prg_i$ which has program code that carries out the method according to an embodiment of the invention for evaluation of the tomographic data. If required, a program such as this can also be involved in control of the CT system 1, for example by appropriate tilting of the gantry with respect to the system axis 9.

As illustrated in FIG. 1, it is also possible for the control and computation unit 10 of the CT system 1 to be connected to a data bus 14, to which, in turn, one or more workstations 12 with their own memory 13 are connected. Image evaluations for the purposes of an embodiment of the invention could then be carried out in these workstations 12 without influencing the work of the CT system. For example, once the tomographic image data has been transmitted to a workstation 12 such as this, the desired slice planes can be defined automatically here, and the slice planes can be displayed.

FIGS. 2 and 3 respectively show a side view and a coronal view of a complete spinal column. To assist orientation, the figure shows the annotations of the individual vertebrae HW1 to HW7 (cervical spine) TH1 to TH12 (thoracic spine) and LW1 to LW5 (lumbar spine). In addition, the scan area of the CT 15 for this patient is shown, by way of example, as a quadrilateral represented by dashed lines, so that the actual image processing and determination of the relevant slice planes are carried out in this area. By way of example, this illustration shows the automatically determined slice planes of the intervertebral area with the slice plane packs Z1 to Z10, covering the area from the sixth cervical vertebra HW6 to the ninth thoracic vertebra TH9. As can be seen from the illustration, it is not possible in this case to use a single slice plane and, instead, a new orientation of the slice planes must be determined for each individual intervertebral area, to be precise not only in the side view but additionally also in the coronal view, as can be seen from FIG. 3. Manual selection of the slice planes in this way is complex and may lead to undesirable waiting times on the CT or, in general, on the tomography system.

It should be noted that the slice image areas illustrated in the figures may also in practice be further away from one another, and/or a greater number of slice image areas may be produced so that the packs of slice image areas extend further into the vertebrae.

The image-processing mechanisms for automatic definition of the desired slice planes, for example in the intervertebral area—as is illustrated in FIGS. 2 and 3—are in principle generally known. Nevertheless, by way of example, FIG. 4 shows a variant for defining the optimum intermediate plane. FIG. 4 shows an X-ray image of an intervertebral area with an upper vertebra TH1 and the vertebra TH2 below it. The center plane M is now defined by determining a multiplicity of distance lines a1 to a5 between the ventral plate of the vertebra TH1 and the dorsal plate of the vertebra TH2, whose center point is defined, and by defining a central intervertebral plane Z which is statistically favorable approximates the center points of the distance lines a1 to a5. This method may, of course, be carried out not just on one plane and, in fact the distance lines may also be determined in the space between the dorsal plate and the ventral plate so that, overall, a center plane Z is calculated which comes as close as possible to an angle-bisecting plane between the ventral plate and dorsal plate of adjacent vertebrae.

Figure 5:
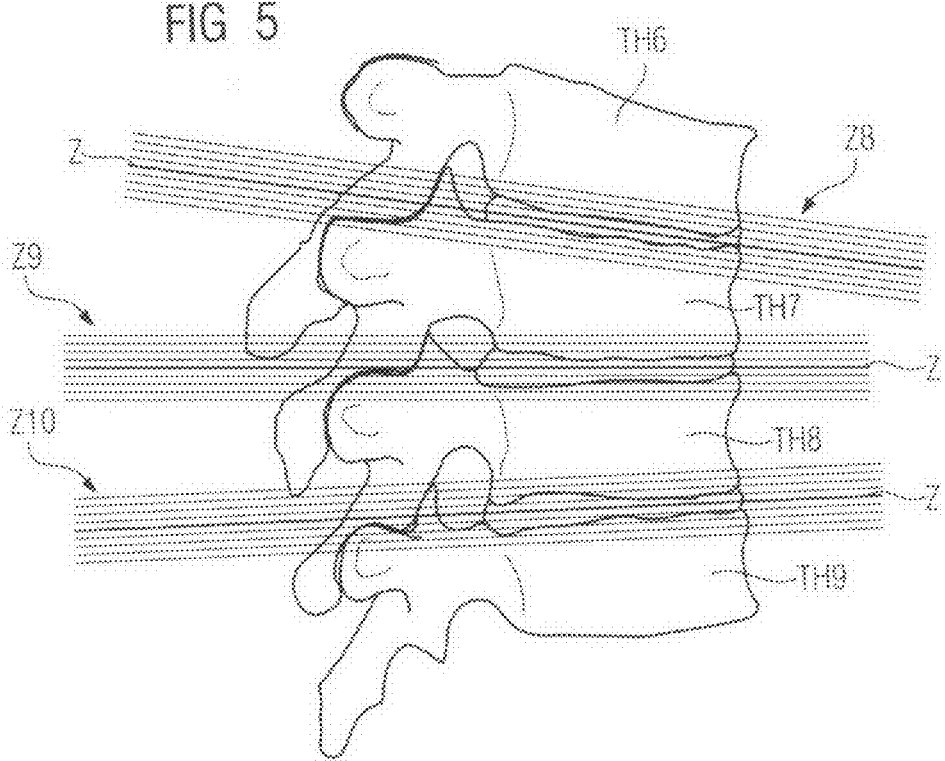
FIG. 5: shows an illustration of axial slice planes with vertebrae, in a detailed view of four vertebrae TH9 to TH6.

A result such as this is illustrated, once again in FIG. 5, in an enlarged form. This figure shows the vertebrae TH6 to TH9. The central intervertebral planes Z—illustrated somewhat bolder—are shown between the vertebrae, and the intervertebral slice image areas are automatically entered, parallel to these planes Z, at equal intervals in packs Z8 to Z10.

These intervertebral slice image areas entered in this way can then either be expressed for actual diagnostic purposes or can be displayed on a screen for the doctor. According to an embodiment of the invention, the respectively sliced vertebra and/or the details of the adjacent vertebrae can additionally be overlaid on a slice image area such as this.

Figure 6:
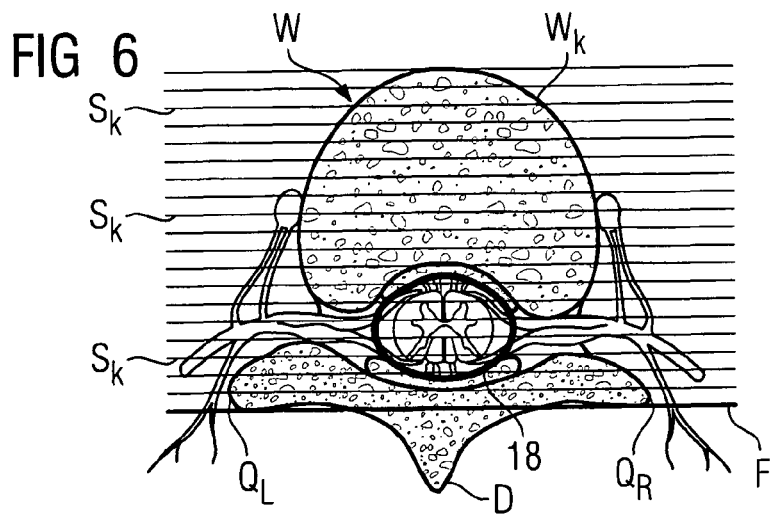
FIG. 6: shows an illustration of an axial slice of a vertebra with automatically applied coronal slice images.

FIG. 6 shows an axial slice through a vertebra, comprising the vertebral body $W_k$, the transverse processes $Q_L$, $Q_R$ arranged on the left and right-hand sides, and the spinous process D. The figure also shows the spinal canal 18, running centrally in the vertebra. On the basis of the inventor's ideas, coronal slices are automatically now placed through the individual vertebrae for indication of diagnostic relevance. This is done by defining a frontal line, connecting the two transverse processes $Q_L$ and $Q_R$ to one another at the edge and thus providing a first orientation for the coronal slice areas. In addition, the orientation of the center plane M—illustrated in FIG. 8—is defined between the dorsal plate and the ventral plate of the vertebral body, and the plane which is at right angles to this and runs parallel to the orientation of the connecting line between the transverse processes is used as the coronal slice plane K.

A multiplicity of coronal slice image areas $S_k$ are automatically produced, preferably at equal intervals, parallel to this coronal slice area F, passing through the vertebra, and showing it completely, largely filling the format and preferably all to the same scale.

Figure 7:
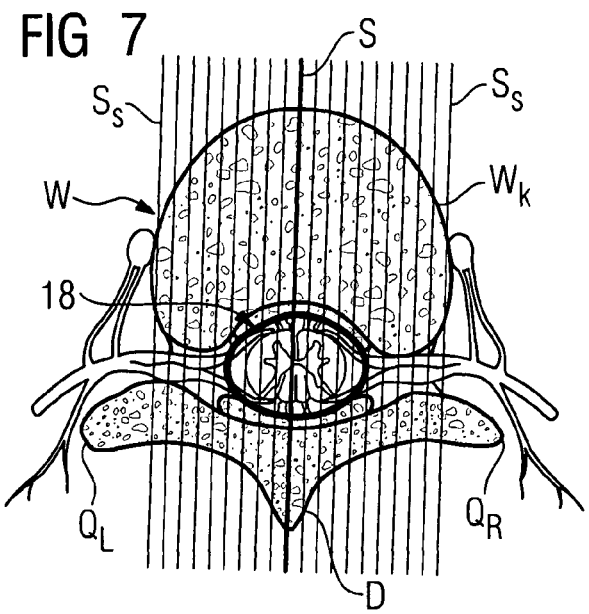
FIG. 7: shows an axial section of a vertebra with automatically applied sagittal slice images.
Figure 8:
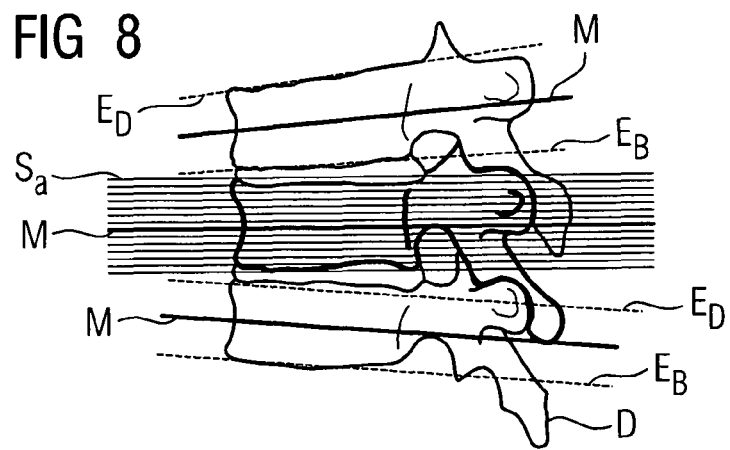
FIG. 8: shows an illustration of the vertebra from FIGS. 6 and 7 in the form of a side view with axial slices through the entire vertebra.

FIG. 7 shows sagittal slice image areas $S_s$ which are defined automatically by once again determining the center plane M—illustrated in FIG. 8—between the ventral plate and dorsal plate of the vertebral body $W_k$ for the vertebra under consideration. Furthermore, the longitudinal axis of the spinous process D is defined which, by definition, runs parallel to the sagittal slice plane S. The sagittal slice plane S is defined completely by the fact that it runs at right angles to the center plane M and parallel to the longitudinal axis of the spinous process D of the vertebra. The sagittal slice image areas $S_s$ are defined parallel to this. The entire set of sagittal slice image areas $S_s$ is then distributed at equal intervals over the vertebra, so that the illustrations calculated in these slice image areas $S_s$ indicate the vertebra completely, largely filling the format and preferably all to the same scale.

If the aim is to display axial slices of the selected vertebra, then the procedure shown in FIG. 8 is adopted. By way of example, FIG. 8 shows three vertebra arranged one above the other, with the central vertebra being intended to correspond to the axially displayed vertebra from FIGS. 6 and 7. This vertebra likewise has an upper dorsal plate and a lower ventral plate, which respectively define a plane $E_D$ and $E_B$. The central angle-bisecting plane M between these planes $E_D$ and $E_B$ corresponds, according to an embodiment of the invention, to the axial plane of the vertebra. The axial slice image areas $S_a$ of the vertebra are therefore defined to be parallel to and at equal distances from this axial slice plane M over the entire vertebra so that, in this case as well, the slice image areas can display the vertebra completely, and largely fill in the format for optimum diagnosis. FIG. 8 shows the axial slice planes M of the upper and lower vertebrae, additionally showing the central planes $E_D$ and $E_B$ of the respective dorsal plate and ventral plate, in the form of dashed lines. For clarity, the planes $E_D$ and $E_B$ have been omitted for the central vertebra.

Once again, it should be noted that the direction details referred to in an embodiment of the invention, such as axial, coronal and sagittal, in each case relate to the bone structure under consideration and not, in the normally general manner, to the patient and the patient's longitudinal axis. Since these bone structures are generally arranged at an angle to the patient's longitudinal axis, the abovementioned planes are also arranged obliquely relative to the patient.

If the slice image planes described in FIGS. 2 to 8 are now determined automatically, then the doctor is provided with all the relevant slice images which he requires for optimum diagnosis of the spinal column. The scope of an embodiment of the invention also covers all of the slice image planes described here being determined in a generalized form but not automatically, with only those slice image planes which are relevant for the diagnostic question being determined.

Figure 9:
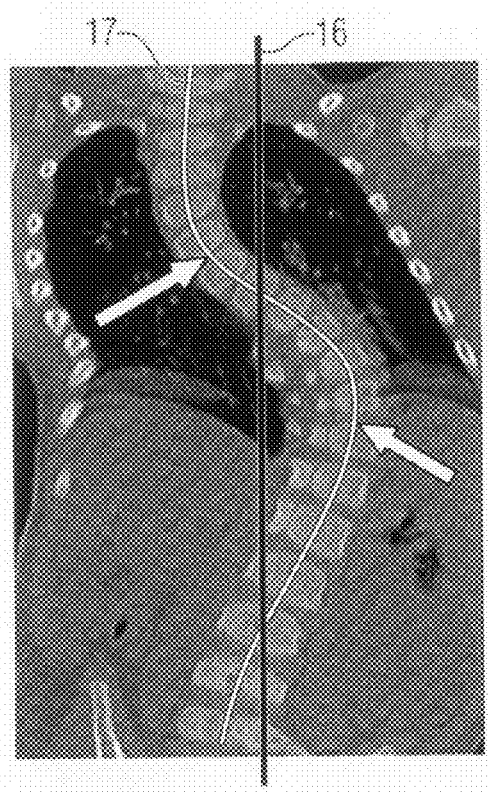
FIG. 9: shows a coronal slice through a spinal column with severe scoliosis, illustrating the profile of an automatically calculated center line of the vertebrae.

FIGS. 9 to 11 now once again describe a further problem relating to spinal column diagnosis. In this case, the aim is on the one hand to cover the spinal canal of the spinal column and on the other hand the extent on the vertebral bodies jointly in one image. This is problematic, for example, in the case where the patient has severe scoliosis. In this case, the spinal column is severely curved transversely, so that a patient-related sagittal slice through 16—as is shown in FIG. 9—would not display all the vertebrae in the spinal column. The inventor accordingly proposes that the center line 17 be defined automatically by the individual vertebral bodies with an image then being produced which covers a slice along the center line through the vertebral bodies on one plane.

Figure 10:
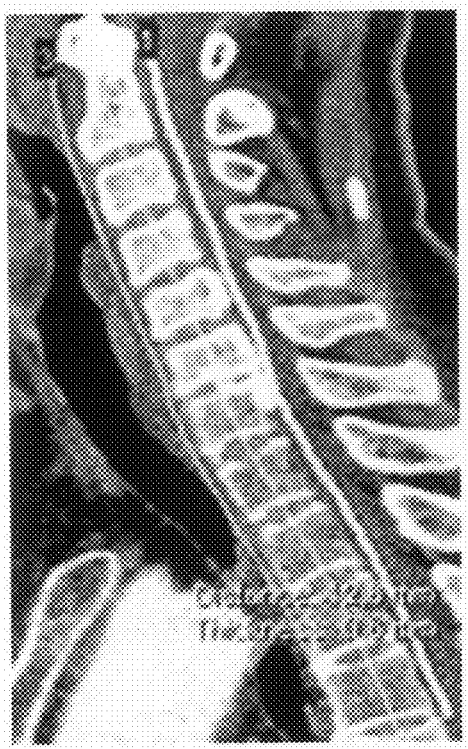
FIG. 10: shows a sagittal slice through a curved cervical spine, similar to FIG. 9, covering the center line in the slice image plane and being marked by boundaries.

One such image is shown by way of example in FIG. 10 in which an image which displays all the cervical vertebrae and some of the thoracic vertebrae on one slice plane has been produced despite severe curvature of the spinal column.

Figure 11:
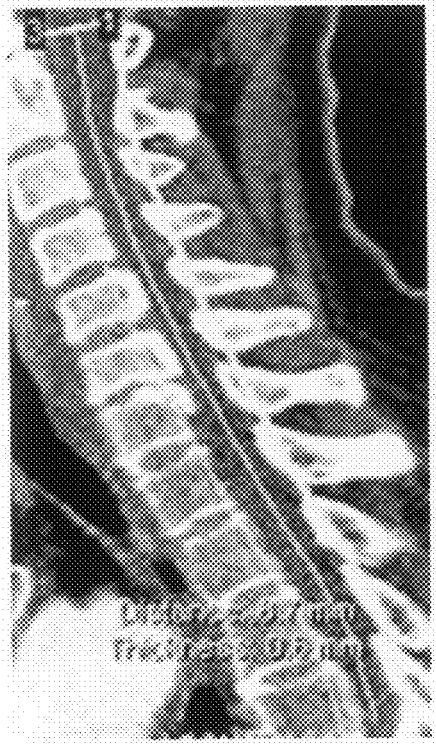
FIG. 11: shows a similar illustration to that in FIG. 10, but with the spinal canal being marked.

In a corresponding manner, it is also possible to define the center line of the spinal canal in the individual vertebrae rather the center line of the vertebral bodies and in this case as well to define a curved slice through this and to display this as a planar slice image, as is shown in FIG. 11.

This production of slice image areas as shown in FIG. 10 for the vertebral bodies or, as shown in FIG. 11, for the spinal canal, can be carried out automatically, thus drastically reducing the manual work on the screen.

Thus, overall, the invention provides a capability which allows the workflow for spinal column diagnosis to be drastically automated, with the processing time per spinal column section being reduced from about five minutes to one minute. Less well-versed users can therefore also quickly produce a satisfactory result since the automation is dependent on only a relatively low level of specialist knowledge. The method described above can be carried out both in conjunction with CT data and with tomographic data from magnetic-resonance examinations or other tomographic examinations.

It is self-evident that the features of embodiments of the invention mentioned above can be used not only in the respectively stated combination but also in other combinations or on their own without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatic determination from a tomographic image data record of a patient, comprising:

scanning the patient using a tomography system;

reconstructing a three-dimensional tomographic image data record of at least a part of the patient from the scanning;

determining a spatial position and orientation of vertebrae of the patient;

defining a diagnostic question, in which the structure of a vertebra is itself important, the defining including, determining a position of end points of a transverse processes of the vertebra, determining planes of a dorsal plate and ventral plate and of an angle-bisecting plane between the dorsal plate and the ventral plate, determining a plane parallel to a connecting line between the end points of the transverse processes and perpendicular to a central interplate plane, and calculating a multiplicity of slice image surfaces parallel to a coronal plane;

automatically determining medically relevant slice image areas based on the defining; and creating and displaying slice images of the automatically determined medically relevant slice image areas, wherein the vertebrae are automatically annotated in at least one of at least one topogram and the three-dimensional tomographic image data record, and the automatic annotation of the vertebrae is applied to a manual definition of a vertebra.

2. The method as claimed in claim 1, wherein the slice images of the automatically determined medically relevant slice image areas are stored on a patient-specific basis.

3. The method as claimed in claim 1, wherein the position, orientation and extent of the automatically determined medically relevant slice image areas are stored.

4. The method as claimed in claim 3, wherein a reference to the tomographic image data record is stored.

5. The method as claimed in claim 3, wherein a reference to the original detector data, from which the tomographic image data record was reconstructed, is stored.

6. The method as claimed in claim 1, wherein the defining of the diagnostic question, for which an intervertebral area possibly with adjacent dorsal and ventral plates of the adjacent vertebrae is important, comprises:

determining an orientation of the ventral plate of an upper vertebra located at or near a top of the spine of the patient;

determining an orientation of the dorsal plate of a lower vertebra located at or near bottom of the spine of the patient;

determining an orientation of an angle-bisecting plane between a previously determined ventral and dorsal plate; and calculating a multiplicity of slice image areas parallel to the angle-bisecting plane.

7. The method as claimed in claim 6, wherein two outer intervertebral slice image areas each intersect the adjacent vertebra.

8. The method as claimed in claim 7, wherein at least one slice image area is additionally calculated which runs parallel to and through the ventral plate of the upper vertebra.

9. The method as claimed in claim 6, wherein at least one slice image area is additionally calculated which runs parallel to and through the dorsal plate of the lower vertebra.

10. The method as claimed in claim 6, wherein at least one slice image area is additionally calculated which runs parallel to and through the ventral plate of the upper vertebra.

11. The method as claimed in claim 1, wherein the multiplicity of slice image surfaces parallel to the coronal plane completely surround the vertebra.

12. The method as claimed in claim 1, wherein the defining of the diagnostic question, for which the structure of a vertebra is itself important, comprises:

determining planes of a dorsal plate and ventral plate of the angle-bisecting plane between the dorsal plate and the ventral plate; and calculating a multiplicity of slice image areas parallel to the axial interplate plane.

13. The method as claimed in claim 12, wherein the multiplicity of axial vertebra slice image areas completely surround the vertebra.

14. The method as claimed in claim 1, wherein the defining of the diagnostic question, in which the structure of a vertebra is itself important, comprises:

determining a longitudinal axis of a spinous process of the vertebra;

determining a plane at right angles to an axial interplate plane and parallel to the longitudinal axis of the spinous process; and calculating a multiplicity of slice image areas parallel to a sagittal vertebral plane.

15. The method as claimed in claim 14, wherein the multiplicity of sagittal vertebra slice image areas completely surround the vertebra with the exception of the transverse processes.

16. The method as claimed in claim 14, wherein one of the sagittal vertebra slice image areas runs through the spinous process.

17. The method as claimed in claim 1, wherein the slice image areas of each relevant slice plane are arranged at equal intervals.

18. The method as claimed in claim 1, wherein distances between all the slice image areas of each slice plane are the same over all the slice planes.

19. The method as claimed in claim 1, wherein the defining of a diagnostic question, in which a spinal canal is important, comprises:

determining a position of a center of the spinal canal, in a plurality of selected vertebrae;

determining a position of the longitudinal axes of the spinous processes of the selected vertebrae;

determining a center plane through the longitudinal axis of the spinous processes and the positions of the center of the spinal canals of the selected vertebrae; and calculating at least one slice image area along the central sagittal spinal plane.

20. The method as claimed in claim 19, further comprising a multiplicity of preferably equidistant sagittal slice image areas parallel to the central sagittal spinal plane.

21. The method as claimed in claim 1, wherein the defining of a diagnostic question, in which the spinal column overall is important, comprises:

determining a position of the center of the vertebrae;

determining a position of the longitudinal axes of the spinous processes of the vertebrae;

determining a central plane through the longitudinal axis of the spinous processes and the positions of the center of the vertebrae; and calculating at least one slice image area along the central sagittal vertebral plane.

22. The method as claimed in claim 21, further comprising a multiplicity of preferably equidistant sagittal slice image areas parallel to the central sagittal vertebral plane.

23. The method as claimed in claim 1, wherein the slice image areas are of such a size that the at least one vertebra to be displayed is displayed such that it fills at least 50% of the format.

24. The method as claimed in claim 23, wherein the slice image areas are of such a size that the at least one vertebra to be displayed is displayed such that it fills at least 75% of the format.

25. The method as claimed in claim 1, wherein the automatic annotation of the vertebrae is transferred to the vertebrae shown in the slice area images.

26. The method as claimed in claim 1, wherein, when viewing the slice image areas on a screen display, an operator is provided with a capability to scroll through the automatically determined planes.

27. The method as claimed in the preceding patent claim 26, wherein, while scrolling through, the currently displayed slice is also displayed in an overview illustration of the spinal column, in addition to the slice image area.

28. The method as claimed in claim 1, wherein the automatically determining of medically relevant slice areas includes automatically determining of medically relevant slice areas of the reconstructed three-dimensional tomographic image data record and wherein the automatically determining medically relevant slice areas is done in accordance with a previously defined diagnostic question relating to position, orientation and extent for spinal column diagnosis and in accordance with the determined spatial position and orientation of vertebrae of the patient.

29. A tomography system, comprising:
   a computation and control unit, including a memory to store program code, the program code being useable to carry out, when executed on the computation and control unit, the method steps as claimed in claim 1 during operation.

30. A screen workstation, comprising:
   a computation and control unit, including a memory to store program code, the program code being useable to carry out, when executed on the computation and control unit, the method steps as claimed in claim 1 during operation.

31. A non-transitory computer readable medium including program segments for, when executed on a computer device, causing the computer device to implement the method of claim 1.

32. An apparatus for automatic determination from a tomographic image data record of a patient, comprising:
   means for scanning the patient using a tomography system;
   means for reconstructing a three-dimensional tomographic image data record of at least a part of the patient from the scanning;
   means for determining a spatial position and orientation of vertebrae of the patient;
   means for automatically determining medically relevant slice areas in accordance with a defined diagnostic question relating to position, orientation and extent for spinal column diagnosis; and
   means for creating and displaying slice images of the automatically determined medically relevant slice image areas, wherein
      the vertebrae are automatically annotated in at least one of at least one topogram and the three-dimensional tomographic image data record, and
      the automatic annotation of the vertebrae is applied to a manual definition of a vertebra.

33. The apparatus of claim 32, wherein the apparatus is a tomography system.

34. The apparatus of claim 32, wherein the apparatus is a screen workstation.

* * * * *